US011771337B2

(12) United States Patent
Eichler et al.

(10) Patent No.: US 11,771,337 B2
(45) **Date of Patent: *Oct. 3, 2023**

(54) MAGNETIC FIELD GENERATOR WITH MINIMAL IMAGE OCCLUSION AND MINIMAL IMPACT ON DIMENSIONS IN C-ARM X-RAY ENVIRONMENTS

(71) Applicant: St. Jude Medical International Holding S.à r.l., Luxembourg (LU)

(72) Inventors: Uzi Eichler, Haifa (IL); Alon Izmirli, Ganot Hadar (IL); Yuval Vaknin, Hanaton (IL); Kobi Kor, Ramat Hsharon (IL)

(73) Assignee: ST JUDE MEDICAL INTERNATIONAL HOLDING S.A.R.L., Luxembourg (LU)

( * ) Notice: Subject to any disclaimer, the term of this patent is extended or adjusted under 35 U.S.C. 154(b) by 1160 days.

This patent is subject to a terminal disclaimer.

(21) Appl. No.: 16/403,194

(22) Filed: May 3, 2019

(65) Prior Publication Data

US 2019/0313939 A1 Oct. 17, 2019

Related U.S. Application Data

(63) Continuation of application No. 15/034,474, filed as application No. PCT/IB2014/065497 on Oct. 21, 2014, now Pat. No. 10,321,848.

(Continued)

(51) Int. Cl.

| | |
|---|---|
| ***A61B 5/06*** | (2006.01) |
| ***A61B 6/00*** | (2006.01) |
| ***A61B 34/20*** | (2016.01) |

(52) U.S. Cl.

CPC ............ *A61B 5/062* (2013.01); *A61B 6/4441* (2013.01); *A61B 6/503* (2013.01); *A61B 34/20* (2016.02);

(Continued)

(58) Field of Classification Search

CPC ....... A61B 5/062; A61B 6/4441; A61B 6/503; A61B 34/20; A61B 6/487;

(Continued)

(56) References Cited

U.S. PATENT DOCUMENTS

| | | | | |
|---|---|---|---|---|
| 512,340 A | | 1/1894 | Tesla | |
| 5,913,820 A | * | 6/1999 | Bladen .................. | A61B 34/20 600/407 |

(Continued)

FOREIGN PATENT DOCUMENTS

| | | |
|---|---|---|
| CN | 1681448 A | 10/2005 |
| EP | 0483698 A1 | 5/1992 |

(Continued)

*Primary Examiner* — Sanjay Cattungal
(74) *Attorney, Agent, or Firm* — Billion & Armitage

(57) ABSTRACT

A magnetic field generator assembly is configured to be associated with a table supporting a body. The magnetic field generator comprises magnetic field transmitters that are thin (of minimal height) and transparent, or substantially transparent, to x-ray radiation. The magnetic field transmitters are configured to minimally obstruct components of an imaging system and to minimally interfere with image quality.

21 Claims, 5 Drawing Sheets

44 45 57A 21 20 62 64

Related U.S. Application Data

(60) Provisional application No. 61/900,846, filed on Nov. 6, 2013.

(52) U.S. Cl.
CPC ....... *A61B 6/487* (2013.01); *A61B 2034/2051* (2016.02); *A61B 2562/17* (2017.08)

(58) Field of Classification Search
CPC ........ A61B 2034/2051; A61B 2562/17; A61B 5/0035; A61B 5/0036; A61B 5/0044
See application file for complete search history.

(56) References Cited

U.S. PATENT DOCUMENTS

| | | | | |
|---|---|---|---|---|
| 5,944,023 | A | 8/1999 | Johnson et al. | |
| 6,177,792 | B1 | 1/2001 | Govari et al. | |
| 6,368,285 | B1 | 4/2002 | Osadchy et al. | |
| 6,493,573 | B1 * | 12/2002 | Martinelli | A61B 34/20 324/257 |
| 6,534,970 | B1 * | 3/2003 | Ely | G01D 5/2086 324/207.17 |
| 6,707,298 | B2 * | 3/2004 | Suzuki | G01R 33/093 324/252 |
| 6,757,557 | B1 * | 6/2004 | Bladen | A61B 34/20 324/207.17 |
| 6,856,823 | B2 | 2/2005 | Ashe | |
| 7,386,339 | B2 | 6/2008 | Strommer et al. | |
| 8,847,587 | B2 | 9/2014 | Govari et al. | |
| 9,024,624 | B2 | 5/2015 | Brunner | |
| 9,662,487 | B2 * | 5/2017 | Kveen | A61N 1/362 |
| 2003/0233042 | A1 | 12/2003 | Ashe | |
| 2007/0135803 | A1 * | 6/2007 | Belson | A61B 1/00154 606/1 |
| 2007/0197899 | A1 * | 8/2007 | Ritter | A61B 5/062 600/407 |
| 2007/0244388 | A1 * | 10/2007 | Sato | A61B 5/062 600/550 |
| 2008/0018307 | A1 | 7/2008 | Strommer et al. | |
| 2008/0183071 | A1 | 7/2008 | Strommer et al. | |
| 2009/0045905 | A1 * | 2/2009 | Nakagawa | H01F 17/0006 336/232 |
| 2009/0082989 | A1 | 3/2009 | Zuhars et al. | |
| 2009/0233042 | A1 | 9/2009 | Sadato et al. | |
| 2009/0243780 | A1 * | 10/2009 | Inoue | H01L 23/645 336/200 |
| 2010/0109848 | A1 | 5/2010 | Blair et al. | |
| 2010/0305427 | A1 | 12/2010 | Huber et al. | |
| 2011/0224537 | A1 | 9/2011 | Brunner | |
| 2012/0029343 | A1 | 2/2012 | Wasson et al. | |
| 2013/0026279 | A1 * | 1/2013 | Agrikli | H02K 41/0356 242/476.7 |
| 2014/0039302 | A1 * | 2/2014 | Miller | H01R 24/86 361/752 |
| 2014/0188133 | A1 * | 7/2014 | Misener | A61B 8/0833 606/130 |
| 2014/0200556 | A1 * | 7/2014 | Sela | A61M 25/0127 604/528 |
| 2014/0275998 | A1 | 9/2014 | Eichler et al. | |
| 2015/0173643 | A1 | 6/2015 | Govari et al. | |
| 2015/0216490 | A1 | 8/2015 | Ashe | |
| 2017/0087333 | A1 | 3/2017 | Sela et al. | |

FOREIGN PATENT DOCUMENTS

| | | | |
|---|---|---|---|
| JP | H03280511 | A | 12/1991 |
| JP | 2002153443 | A | 5/2002 |
| JP | 200878686 | A | 8/2008 |
| WO | 2004006795 | A1 | 1/2004 |
| WO | 2004061460 | A3 | 7/2005 |
| WO | 2012/090148 | A1 | 7/2012 |
| WO | 2015068069 | A1 | 5/2015 |

* cited by examiner

MAGNETIC FIELD GENERATOR WITH MINIMAL IMAGE OCCLUSION AND MINIMAL IMPACT ON DIMENSIONS IN C-ARM X-RAY ENVIRONMENTS

CROSS-REFERENCE TO RELATED APPLICATIONS

This application is a continuation of U.S. application Ser. No. 15/034,474, filed 4 May 2016 (the '474 application), now U.S. Pat. No. 10,321,848, which is a national stage filing based upon international application no. PCT/IB2014/065497, filed 21 Oct. 2014 (the '497 application), which claims the benefit of U.S. provisional application No. 61/900,846, the 6 Nov. 2013 (the '846 application). The '474 application, the '497 application, and the '846 application are all hereby incorporated by reference in their entirety as though fully set forth herein.

BACKGROUND a. Field

The present disclosure relates to a magnetic field generator with relatively thin magnetic field transmitters configured to, among other things, minimally occlude a fluoroscopic image.

b. Background

A wide variety of medical devices may be inserted into the body to diagnose and treat various medical conditions. Catheters, for example, are used to perform a variety of tasks within human bodies and other bodies, including the delivery of medicine and fluids, the removal of bodily fluids, and the transport of surgical tools and instruments. In the diagnosis and treatment of atrial fibrillation, for example, catheters may be used to deliver electrodes to the heart for electrophysiological mapping of the surface of the heart and to deliver ablative energy to the surface of the heart.

Catheters are typically routed to a region of interest through the body's vascular system. In a conventional catheterization, a micro-puncture needle (e.g., a Seldinger needle) is used to puncture the skin surface to gain access to, for example, a femoral artery, and a guide wire is then inserted through the needle before the needle is removed. A catheter sheath with a dilator inserted in it is then inserted over the guide wire. The dilator and the guide wire are then removed, leaving the sheath in place in the femoral artery. The sheath has an inner diameter greater than the outer diameter of a catheter to be used in the procedure. The catheter is then inserted into the sheath, and the sheath and/or catheter are subsequently threaded through the vasculature to a region of interest. Typically, but not necessarily, the catheter is then moved longitudinally relative to the sheath so as to extend from the distal end of the sheath to the region of interest. The longitudinal movement may be done either manually by a clinician or through the use of electromechanical drive systems.

It is desirable to track the position of medical devices such as catheters as they are moved within the body so that, for example, drugs and other forms of treatment are administered at the proper location and medical procedures can be completed more efficiently and safely. One conventional means to track the position of medical devices within the body is fluoroscopic imaging. Fluoroscopy is disadvantageous, however, because it subjects the patient and physician to undesirable levels of electromagnetic radiation. As a result, medical device navigation systems have been developed to track the position of medical devices within the body. These systems typically rely on the generation of electrical or magnetic fields and the detection of induced voltages and currents on position sensors attached to the medical device and/or external to the body. The information derived from these systems is then provided to a physician through, for example, a visual display. Oftentimes, a representation of the medical device is displayed relative to a computer model or one or more images (including, but not limited to, fluoroscopic images) of the anatomical region in which the device is being maneuvered. In order to display the medical device at the correct location relative to the model or image, the model or image must be registered within the coordinate system of the navigation system.

Magnetic field transmitters may be used in conjunction with a medical device navigation system. The transmitters within the navigation system can be installed in a variety of ways. If the imaging system used to capture the images is physically integrated with the navigation system, as described in commonly assigned U.S. Published Patent Application No. 2008/0183071 A1, the entire disclosure of which is incorporated herein by reference, the transmitters can be installed such that they will not be in the path of the x-ray beam. The foregoing discussion is intended only to illustrate the present field and should not be taken as a disavowal of claim scope.

BRIEF SUMMARY OF THE DISCLOSURE

A magnetic field generator assembly is configured to be associated with a table supporting a body. The magnetic field generator comprises magnetic field transmitters that are thin (of minimal height) and transparent, or substantially transparent, to x-ray radiation. The magnetic field transmitters are adapted to minimally obstruct components of an imaging system and to minimally interfere with image quality.

In accordance with an aspect of the present disclosure, a magnetic field generating apparatus, configured to be associated with a table supporting a body, comprises an elongate conductive element arranged as a curve on a plane, wherein the curve winds around a central axis, extending perpendicular to the curve plane, at a continuously increasing distance from the central axis to an outer periphery of the curve; wherein the conductive element forms a first layer of the apparatus; and wherein the first layer lies in a first plane.

In accordance with another aspect of the present disclosure, a medical device navigation system comprises: a magnetic field generator assembly configured to generate a magnetic field of at least $10^{-10}$ Tesla in close proximity to a body undergoing treatment, wherein the magnetic field generator assembly comprises the following: (i) an elongate conductive element arranged in a planar curve; (ii) a conductive wire connecting the conductive element to a power source; (iii) a control unit capable of controlling current supplied to the conductive element; and (iv) a housing surrounding the conducive element; and wherein the magnetic field generator assembly is also configured to be operatively coupled with the following: (a) a table supporting a body; (b) an imaging system comprising a structure movable relative to the body; and (c) a display.

DETAILED DESCRIPTION

Figure 1:
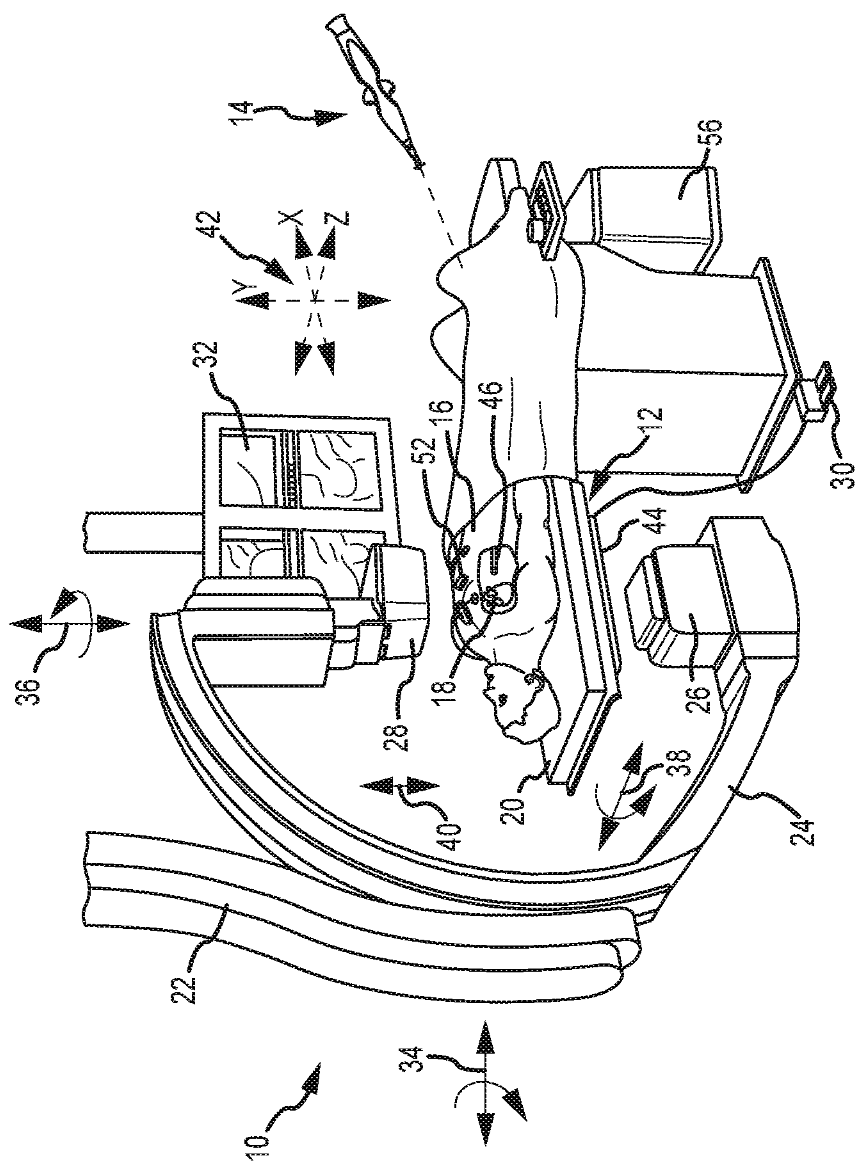
FIG. 1 is a diagrammatic view of a medical device navigation system in accordance with one embodiment of the present teachings.

Referring to the drawings wherein like reference numerals are used to identify identical components in the various views, FIG. 1 illustrates an electrophysiology lab including an imaging system 10 and a system 12 for navigating a medical device 14 relative to and within a region of interest in a patient's body 16 such as the heart 18 in accordance with one embodiment of the present teachings. Device 14 may comprise, for example, an electrophysiological (EP) mapping catheter, an intracardiac echocardiography (ICE) catheter, or an ablation catheter. It should be understood, however, that the inventive system could be used to navigate a variety of diagnostic and treatment devices used to treat various regions of interest within body 16.

Imaging system 10 is provided to acquire images of heart 18 or other anatomical regions of interest and comprises a fluoroscopic imaging system in the illustrated embodiment. System 10 has a structure that is movable relative to the various components of system 12 and relative to body 16 and a table 20 supporting body 16. System 10 may include a number of structural components including, in the illustrated embodiment, a support 22, an arm 24, a radiation emitter 26, and a radiation detector 28. System 10 may also include an electronic control unit (not shown) for controlling operation of system 10 and one or more input devices such as control pedal 30 and output devices such as display 32.

Support 22 provides a means for supporting arm 24 and for moving arm 24, emitter 26, and detector 28 relative to body 16. In the illustrated embodiment, support 22 is suspended from a ceiling in the EP lab. Support 22 may be affixed to rails (not shown) or similar structures and may be moved by mechanical, electrical, or electromechanical devices (not shown). Support 22 may be configured to rotate with arm 24, emitter 26, and detector 28 about an axis 34 to position arm 24, emitter 26, and detector 28 relative to body 16.

Arm 24 provides a means for supporting emitter 26 and detector 28 relative to body 16. Arm 24 may be substantially C-shaped (i.e., a "C-arm") to provide sufficient clearance relative to body 16 and table 20. Arm 24 is configured to rotate in either direction about an axis 36 relative to support 22 to cause corresponding movement of emitter 26 and detector 28 and position emitter 26 and detector 28 relative to body 16 to permit images to be acquired from a variety of angles or orientations.

Emitter 26 is provided to emit electromagnetic radiation (e.g., x-rays) over a field of view between emitter 26 and detector 28 including the anatomical region of interest in body 16. Emitter 26 is disposed at one end of arm 24.

Detector 28 captures electromagnetic radiation passing through the anatomical region of interest in body 16 and generates signals used to create images of the region of interest. In one embodiment, detector 28 may comprise a flat detector and may be configured to rotate about an axis 34 relative to arm 24 and may also be movable relative to arm 24 along an axis 40 to vary the distance between the emitter 26 and detector 28 (i.e., the "source to image" distance or "SID"). Detector 28 is disposed at an opposite end of arm 24 relative to emitter 26.

The relative movement of imaging system 10 and other objects within the electrophysiology lab create various degrees of freedom that system 12 may need to account for as a physician navigates device 14. Arm 24 rotates about axes 34, 36, and 38, and moves along axis 40. Table 20 may move relative to imaging system 10 (or vice versa) in either direction along three orthogonal axes resulting in as many as seven degrees of freedom.

Control pedal 30 provides a means for the physician to control imaging system 10. The physician may, for example, depress pedal 30 to activate radiation emitter 26. Pedal 30 may communicate with an electronic control unit (not shown) for imaging system 10 via a wired or wireless connection.

Display 32 is provided to convey information to a physician to assist in diagnosis and treatment. Display 32 may comprise one or more computer monitors or other display devices. Display 32 may present fluoroscopy images and a graphical user interface (GUI) to the physician. The GUI may communicate a variety of information including, for example, an image of the geometry of heart 18, electrophysiology data associated with the heart 18, graphs illustrating voltage levels over time for various electrodes on medical device 14, and images of medical device 14 and related information indicative of the position of device 14 and other devices relative to the heart 18.

System 12 may be used to determine the position of device 14 within body 16 and within a coordinate system 42 and to navigate device 14 within body 16. System 12 may also be used to determine the positions of other movable objects within the EP lab within coordinate system 42 including body 16 and table 20.

In accordance with one embodiment of the present teachings, system 12 is also used to determine the position of imaging system 10 within coordinate system 42 and, in particular, various components of imaging system 10. System 12 employs magnetic fields and may comprise the system made available under the trademark MediGuide™ by St. Jude Medical, Inc. and generally shown and described in, for example, commonly owned U.S. Pat. No. 7,386,339 and U.S. Patent Application No. 61/787,542, the entire disclosures of which are incorporated herein by reference. System 12 may include a magnetic field generator assembly 44 (shown to better advantage in FIG. 2), means (such as position sensors 46 and 52) for generating information regarding the position of device 14 within body 16 and the position of various objects in the EP lab such as imaging system 10, body 16, and table 20. System 12 may also include an electronic control unit (ECU) 56 and a display such as display 32.

Figure 2:
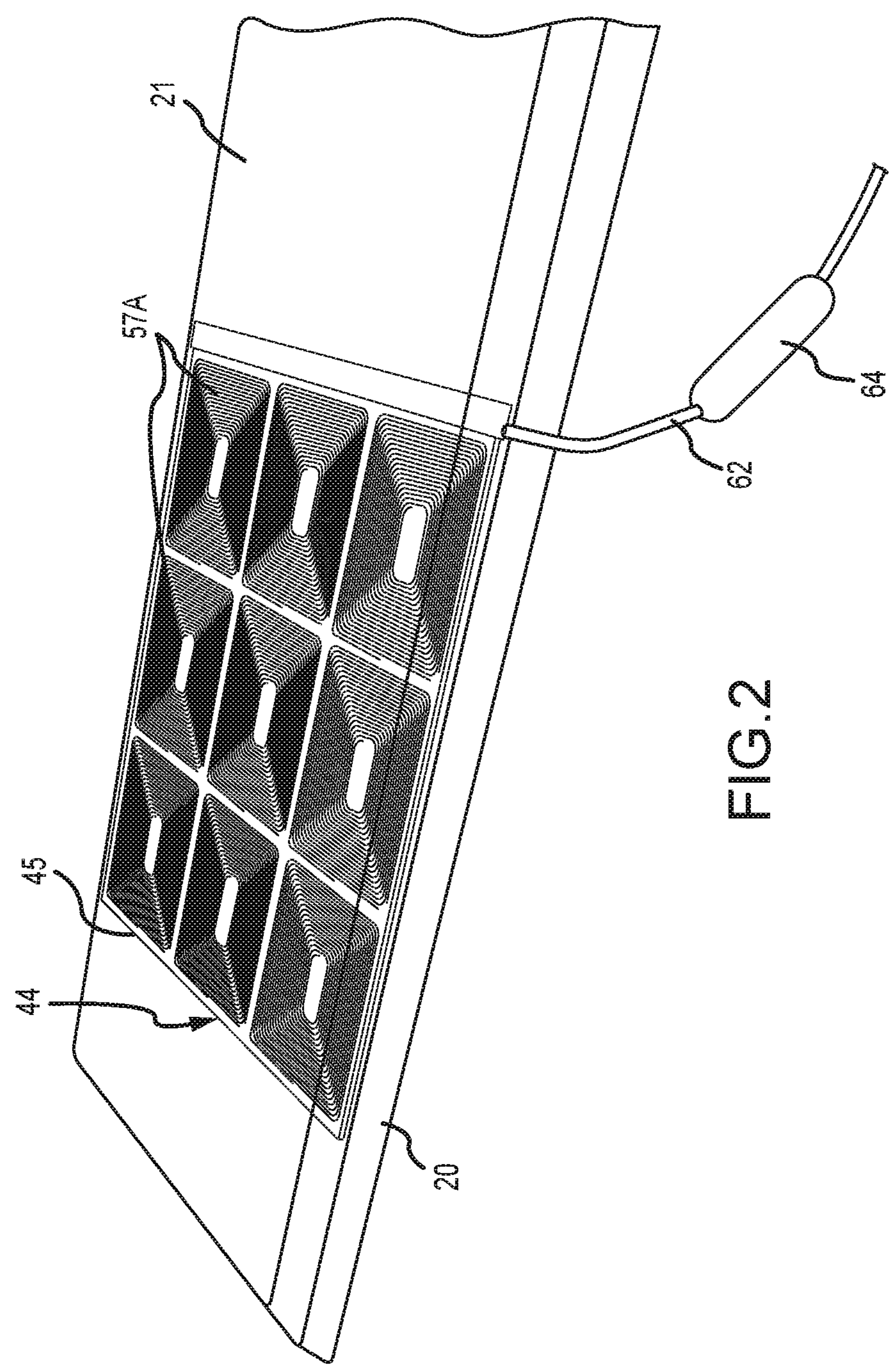
FIG. 2 is a diagrammatic view of the magnetic field generator assembly of the system of FIG. 1.

Generator assembly 44 generates magnetic fields that cause a response in sensors 46 and 52 indicative of the location and orientation of sensors 46 and 52 within the magnetic fields and within coordinate system 42. Generator assembly 44 may be located just beneath table 20, as shown in FIG. 1. Alternatively, generator assembly 44 may be located on top of table 20, such that generator assembly 44 is between a mattress 21 and table (as shown in FIG. 2) and/or between body 16 and table 20. Generator assembly 44 may also be located within table 20 and/or mattress 21. In another embodiment, a generator assembly similar to assembly 44 may be located directly on a patient's body using one or more patches, for example, such as those similar to EnSite™ NavX™ surface electrode patches sold by St. Jude Medical, Inc. Generator assembly 44 may also be installed, so as not to significantly occlude the path of the x-ray beam, in systems where the navigation and imaging systems are physically separate, as described in commonly assigned U.S. Patent Application No. 61/787,542.

Figure 3:
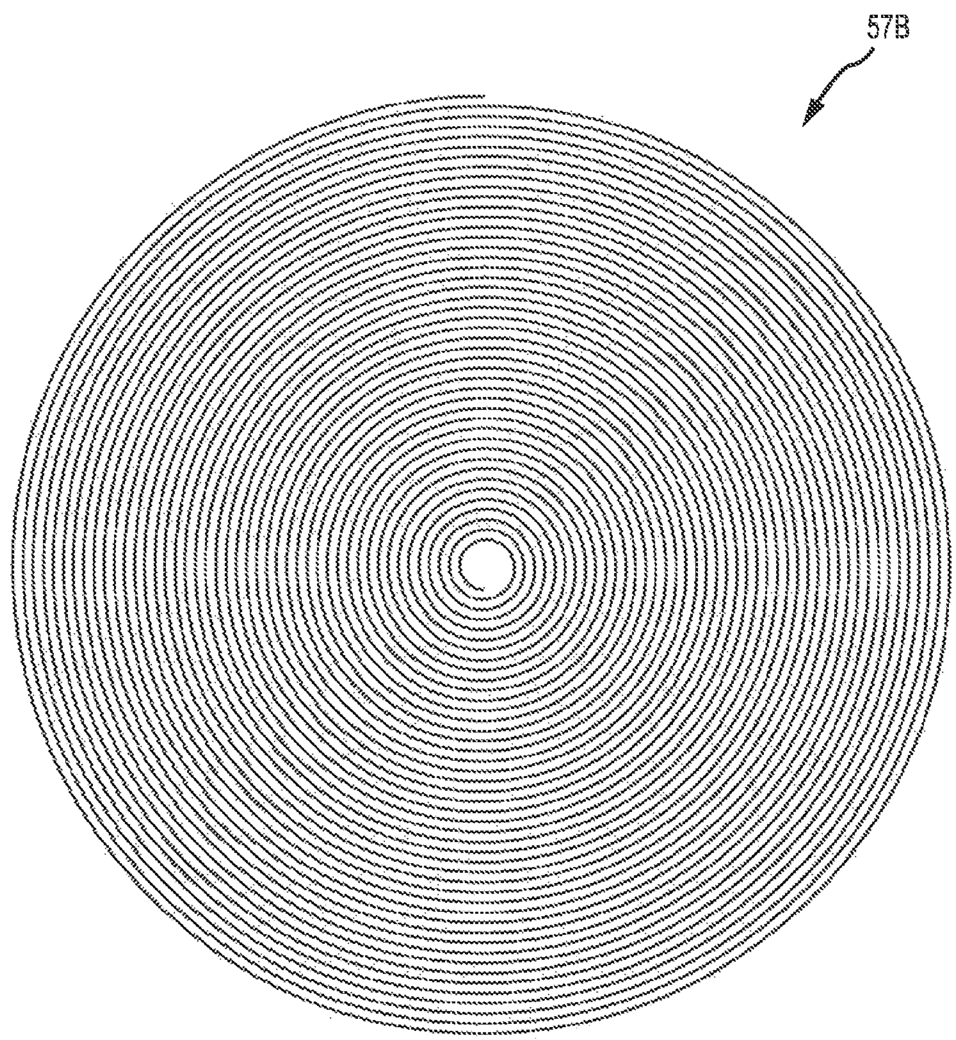
FIG. 3 is a diagrammatic view of a magnetic field transmitter.

Referring to FIG. 2, generator assembly 44 may comprise magnetic field transmitters, such as transmitters 57A, positioned within a housing 45 (or, alternatively, the transmitters may be positioned on the housing). Each transmitter 57A can comprise an elongate conductive element, such as a wire, arranged in a spiral form, such as a coil. The wire gauge used to make the spiral coils of transmitters 57A can be about 0.7 mm (width) by 1 oz. (thickness). The typical length of the wires can be about 20 meters. The separation distance between adjacent turns of the coils of transmitters 57A can be about 0.3 mm The spiral coils of transmitters 57A can be rectangular in shape to occupy the majority of the generator assembly 44 and leave very little space unoccupied, as shown in FIG. 2. Alternatively, transmitters may be circular in shape, as shown at 57B and 57C in FIGS. 3 and 4, respectively. Regardless, in at least one embodiment, the transmitters may be thin and flat, such that they can be easily integrated into or associated with table 20. In an embodiment, the height of each transmitter can typically range from about 10 micrometers to about 0.25 millimeters. Moreover, the distance between the transmitters and the housing 45 that forms the exterior of the generator assembly is minimal, ranging from about 0.2 mm to 2 cm, and the housing 45 may be about 0.2 mm to 2 cm in total height, about 10 cm to 50 cm in total width, and about 10 cm in total length. Thus, generator assembly 44 may be thin and substantially flat. As such, generator assembly 44 may be placed under a mattress 21 or table 20 with minimal or no impact on the geometry of arm 24 and the path in which arm 24 may move relative to bed 20 during a procedure.

Since transmitters according to the disclosed teachings are substantially thin and flat, they also are transparent to, or nearly transparent to, x-rays, which reduces the potential for fluoroscopic interference. As used in this disclosure, “nearly transparent” can mean minimally occlusive (e.g., forming minimal and/or uniform background artifact), or substantially invisible to the human eye, in fluoroscopic images. In an embodiment, transparent or nearly transparent transmitters should not require more radiation to be used in system 10 than would be necessary if the transmitters were absent. As such, transmitters are configured to minimally occlude fluoroscopic images. In an embodiment, transmitters are made from a thin layer of copper or other conductive material. Additionally, transmitters may be encapsulated in x-ray transparent material, such as carbon fiber.

Figure 4:
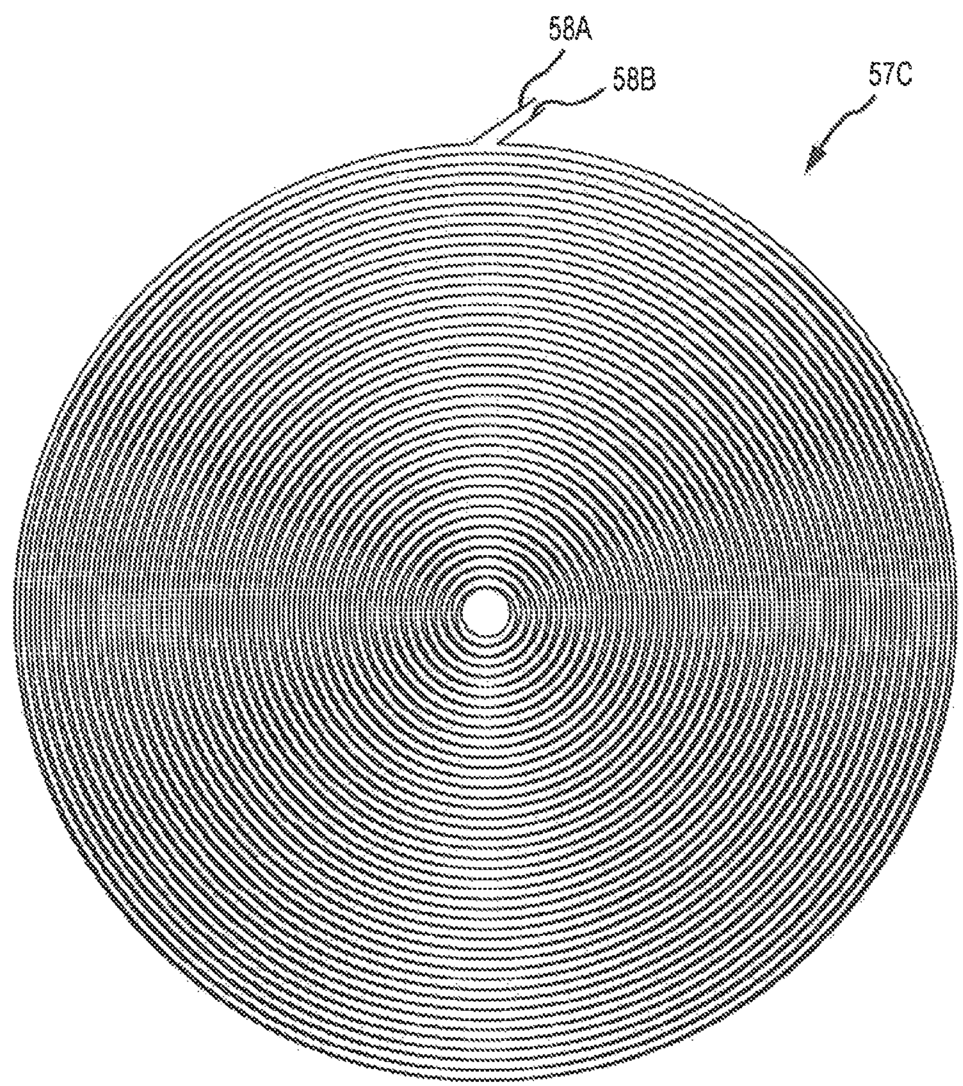
FIG. 4 is a diagrammatic view of a multi-layer magnetic field transmitter.

FIG. 4 shows an example of a transmitter 57C in which the coil has two separate layers. Each layer lies in a separate plane. In an embodiment according to the present teachings, the layers are ‘stacked’ one on top of the other relative to the path between emitter 26 and detector 28 when emitter 26 and detector 28 are oriented as shown in FIG. 1 (i.e., with emitter 26 directly below body 16, and detector 28 directly above body 16). Transmitters can have multiple (e.g., two or more) layers and still be relatively thin and, thus, relatively transparent to the x-rays passing from emitter 26 to detector 28. The two layers of the coil shown in FIG. 4 are both spun in the same direction so as to transmit the magnetic field in a single direction. Furthermore, the coil ends 58A and 58B are located at the same, or near the same, peripheral location 58. Thus, a single ‘thread’ begins at end 58A and forms a first layer, then at the center begins a second layer retracing the path of the first layer, and finally ends at end 58B. Having the coils ends 58A and 58B at the same peripheral location helps reduce parasitical electrical transmission from the power source, which could interfere with the magnetic field.

Figure 5:
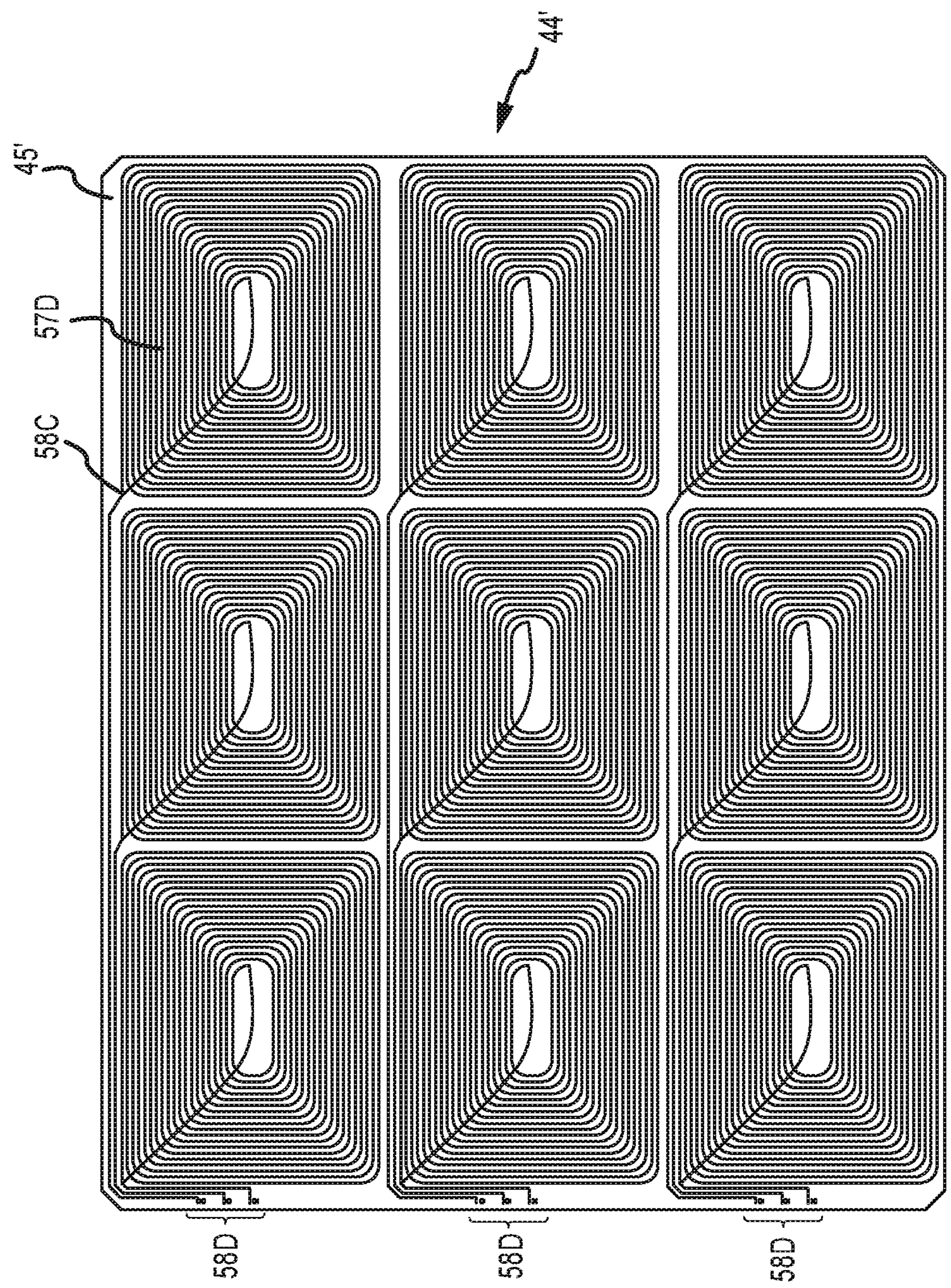
FIG. 5 is a diagrammatic view of a magnetic field generator assembly and its wire connections.

FIG. 5 shows another embodiment of a magnetic field generator assembly 44', similar to assembly 44 shown in FIG. 2, and coil ends 58C and 58D, which ultimately connect to a power source (not shown). In this embodiment, the transmitters 57D can be printed on a substrate or housing 45' using conductive printing ink or printed circuits, for example. The transmitters 57D can be printed on the printed on Each transmitter 57D comprises a coil that begins at end 58C and ends at end 58D (or vice versa). The wiring of the transmitters 57D can be relatively thin and flat, allowing them to be transparent, or nearly transparent, to x-rays. This reduces the potential for fluoroscopic interference attributable to the transmitters 57D. Typically, at the point where coil ends 58C and 58D exit the magnetic field generator assembly 44', they lie close to one another or in a twisted pair configuration. Having only a very small distance between a wire pair and/or twisting the pair helps reduce parasitical electrical transmission form the coils, which could interfere with the magnetic field.

Referring back to FIG. 2, cable 62 provides a means for connecting assembly 44 to ECU 56. Accompanying electronics 64 can be placed on and communicate with cable 62. Accompanying electronics 64 can be used to filter electromagnetic signals going to/from transmitters and resonance circuitry, for example.

Referring again to FIG. 1, position sensors 46 and 52 provide a means for generating information regarding the position of various objects within coordinate system 42. As sensors 46 and 52 move within the magnetic field generated by generator assembly 44, the current output of each sensor 46 and 52 changes thereby indicating the location of sensors 46 and 52 within the magnetic field and within coordinate system 42. Position sensors 46 and 52 may comprise coils. Sensor 46, for example, may be wound about device 14 at or near distal end of device 14, embedded within a wall of device 14, or within a cavity within device 14. Sensors 46 and 52 may also have appropriate insulation and/or shielding (e.g., a conductive foil or wire mesh) to cancel potential interferences from other devices near body 16.

In alternative embodiments, sensors 46 and 52 may comprise any position sensors for detecting changes in magnetic fields including, for example, Hall effect sensors, magnetoresistive sensors, and sensors made from magnetoresistive materials and piezoelectric materials and the like. Sensors 46 and 52 may also be of a type that is able to sense position in one or more (e.g., 1 to 6) degrees of freedom relative to a field generator. Sensors 46 and 52 may communicate position signals to ECU 56 through an interface (not shown) using wires or other conductors, or wirelessly.

In accordance with another embodiment of the present teachings, information regarding the position of imaging system 10 may be obtained based on inputs to or outputs from the imaging system 10. In one embodiment, image data output to display 32 or another destination may be captured and read by ECU 56, and the position of imaging system 10 determined based on fiducial markers in the image or through use of optical character recognition or other techniques for reading character data imprinted on the image and indicative of the position of imaging system 10 or a component thereof, relative to either a prior position of the component or another component of imaging system 10. In particular, the fiducial markers may be embedded in the magnetic field generator assembly 44.

In accordance with yet another embodiment of the present teachings, information regarding the position of imaging system 10 and/or other information associated with imaging system 10 may be obtained by sensing the activation of imaging system 10 and, in particular, the emission of radiation from emitter 26. Radiation emissions may be detected using a radiation detection sensor such as the XB8816 Series sensor offered for sale by X-Scan Imaging Corporation. These sensors maybe embedded in magnetic field generator assembly 44. ECU 56 may be configured to determine a time associate with the radiation emission responsive to a signal generated by the radiation detector sensor and thereby synchronize signals generated by other sensors such as position sensors 46 and 52.

In accordance with yet another embodiment of the present teachings, information regarding the position of imaging system 10 may be obtained by detecting objects, such as anatomical or artificial fiducials, in images generated by system 10 that have a known position within coordinate system 42. In particular, these objects may be embedded in magnetic field generator assembly 44. To limit interference with the physician's view of the anatomy, these objects may have multiple states whereby the objects are visible in some images and invisible in others, or may be generally undetectable to the human eye, but detectable through image processing as described in greater detail in PCT International Publication No. WO 2012/090148 A1, the entire disclosure of which is incorporated herein by reference. In some configurations, the transmitter wiring in magnetic field generator assembly 44 may be undetectable to the human eye, but detectable through image processing.

Although various embodiments have been disclosed above for obtaining positioning information regarding imaging system 10, it should be understood that elements of multiple embodiments could be used in combination. Referring again to FIG. 1, ECU 56 provides a means for determining the position of sensors 46 and 52—and the objects to which sensors 46 and 52 are attached—within coordinate system 42. As discussed below, ECU 56 may further provides a means for registering images generated by imaging system 10 in coordinate system 42 and superimposing images of device 14 on such images, a means for comparing the positions of various objects in the EP lab (such as imaging system 10 and generator assembly 44 or body 16 or table 20) to determine potential physical interference, and/or a means for providing information about the positions of various objects to a physician or other user of system 12. ECU 56 also provides a means for controlling the operation of various components of system 12, including magnetic field generator assembly 44. In embodiments where medical device 14 comprises an electrophysiology or ablation catheter, ECU 56 may also provide a means for controlling device 14 and for determining the geometry of heart 18, electrophysiology characteristics of heart 18 and the position and orientation of device 14 relative to heart 18 and body 16. ECU 56 may also provide a means for generating display signals used to control a display such as display 32. ECU 56 may comprise one or more programmable microprocessors or microcontrollers or may comprise one or more application specific integrated circuits (ASICs). ECU 56 may include a central processing unit (CPU) and an input/output (I/O) interface through which ECU 56 may receive a plurality of input signals including signals generated by sensors 46 and 52, and generate a plurality of output signals including those used to control and/or provide data to magnetic field generator assembly 44 and display 32.

In accordance with the present teachings, ECU 56 may be configured with programming instructions from a computer program (e.g., software) to implement a method for navigating a medical device 14 within body 16. The program may be stored in a computer storage medium such as a memory (not shown) that is internal to ECU 56 or external to ECU 56, and may be pre-installed in the memory or obtained from a computer storage medium external to ECU 56 including from various types of portable media (e.g., compact discs, flash drives, etc.) or file servers or other computing devices accessible through a telecommunications network.

Although several embodiments of a system in accordance with present teachings have been described above with a certain degree of particularity, those skilled in the art could make numerous alterations to the disclosed embodiments without departing from the scope of this disclosure. All directional references (e.g., upper, lower, upward, downward, left, right, leftward, rightward, top, bottom, above, below, vertical, horizontal, clockwise and counterclockwise) are only used for identification purposes to aid the reader's understanding of the disclosed embodiments, and do not create limitations, particularly as to the position, orientation, or use of the disclosed embodiments. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the present teachings as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A magnetic field generating assembly, configured to be associated with a table supporting a body, the assembly comprising:

a plurality of elongate conductive elements arranged in a first plane, wherein each conductive element winds around a central axis, extending perpendicular to the first plane, at a continuously increasing distance from the central axis to an outer periphery of the conductive element;

wherein the plurality of conductive elements forms a first layer of the assembly;

wherein the first layer lies in the first plane; and wherein the plurality of conductive elements each have a width at least 10 times greater than a thickness to minimally obstruct images obtained using x-ray fluoroscopy, where x-rays are passed through the plurality of conductive elements.

2. The assembly of claim 1, wherein the plurality of conductive elements comprises at least three elongate conductive elements.

3. The assembly of claim 1, wherein the plurality of conductive elements comprises at least nine elongate conductive elements.

4. The assembly of claim 1, wherein the plurality of conductive elements further comprises a second layer of the assembly; and wherein the second layer lies in a second plane.

5. The assembly of claim 4, wherein each of the plurality of conductive elements further comprises the first layer and the second layer in a single and continuous manner.

6. The assembly of claim 4, wherein, for each conductive element, the first layer comprises a first inner perimeter and a first outer perimeter, the first outer perimeter defining a first exit point of the conductive element; wherein, for each conductive element, the second layer comprises a second inner perimeter and a second outer perimeter, the second outer perimeter defining a second exit point of the conductive element; and wherein the first exit point and the second exit point are adjacent to each other.

7. The assembly of claim 6, wherein the first layer and the second layer are configured to form a twisted pair at a location peripheral to the first and second exit points.

8. The assembly of claim 1, wherein the plurality of conductive elements further comprises a plurality of layers of the assembly; wherein the plurality of layers lies in a plurality of planes; and wherein the plurality of layers comprises more than two layers.

9. The assembly of claim 1, wherein the plurality of conductive elements is configured to be located above, below, or within the table.

10. The assembly of claim 1, wherein the plurality of conductive elements is configured to be located on the body.

11. The assembly of claim 1, wherein the plurality of conductive elements is configured to be located beneath or within a mattress.

12. The assembly of claim 1, wherein each conductive element is circular or rectangular in shape.

13. The assembly of claim 1, wherein the plurality of conductive elements is positioned within a housing, and wherein the distance between each conductive element and the housing is less than about 2 cm.

14. The assembly of claim 1, configured to be used with an imaging system of a type comprising a structure movable relative to the body.

15. A medical device navigation system comprising:

a magnetic field generator assembly configured to generate a magnetic field of at least $10^{-10}$ Tesla in close proximity to a body undergoing treatment, wherein the magnetic field generator assembly comprises the following:

(i) a plurality of elongate conductive elements arranged in a planar curve, the plurality of conductive elements each having a width at least 10 times greater than a thickness to minimally occlude fluoroscopic images;

(ii) a conductive wire connecting the plurality of conductive elements to a power source;

(iii) a control unit capable of controlling current supplied to the plurality of conductive elements; and (iv) a housing surrounding the plurality of conducive elements; wherein the magnetic field generator assembly is also configured to be operatively coupled with the following:

(a) a table supporting a body;

(b) a fluoroscopic imaging system comprising a structure movable relative to the body; and (c) a display; and wherein the magnetic field generator assembly is configured to minimally occlude fluoroscopic images generated by the fluoroscopic imaging system.

16. The system of claim 15, wherein the magnetic field generator assembly is configured to minimally obstruct movement of the imaging system.

17. The system of claim 15, wherein the magnetic field generator assembly is configured to be located above, below, or within the table.

18. The system of claim 15, wherein a distance between the plurality of conductive elements and a housing surrounding the plurality of conductive elements is less than about 2 cm.

19. The system of claim 15, wherein the plurality of conductive elements forms a first layer, the first layer lying in a first plane; and wherein the plurality of conductive elements forms a second layer, the second layer lying in a second plane.

20. The system of claim 19, wherein each of the plurality of conductive elements further comprises the first layer and the second layer in a single and continuous manner.

21. A magnetic field generating assembly, configured to be associated with a table supporting a body, the assembly comprising:

a plurality of elongate conductive elements arranged in a first plane, wherein each conductive element winds around a central axis, extending perpendicular to the first plane, at a continuously increasing distance from the central axis to an outer periphery of the conductive element;

wherein the plurality of conductive elements forms a first layer of the assembly, the plurality of conductive elements having a flat shape;

wherein the first layer lies in the first plane; and wherein a height of the magnetic field generating assembly is between 10 micrometers to 0.25 mm to be minimally occlusive in fluoroscopic images.

* * * * *